United States Patent
Sano et al.

(10) Patent No.: US 8,597,177 B2
(45) Date of Patent: Dec. 3, 2013

(54) PROBE SHAPE DETECTION APPARATUS AND PROBE SHAPE DETECTION METHOD

(75) Inventors: Daisuke Sano, Yokohama (JP); Hirotaka Akiba, Hino (JP); Hiroyuki Ushifusa, Tama (JP); Kyoko Hiyama, Hachioji (JP); Tomohiko Oda, Kawagoe (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/596,498

(22) Filed: Aug. 28, 2012

(65) Prior Publication Data

US 2013/0060082 A1 Mar. 7, 2013

Related U.S. Application Data

(63) Continuation of application No. PCT/JP2011/064225, filed on Jun. 22, 2011.

(30) Foreign Application Priority Data

Jul. 1, 2010 (JP) .................................. 2010-151410

(51) Int. Cl.
*A61B 1/00* (2006.01)

(52) U.S. Cl.
CPC .................................. *A61B 1/00158* (2013.01)
USPC .......................................... 600/117; 600/424

(58) Field of Classification Search
USPC ............ 600/117, 118, 424; 335/219; 324/219
See application file for complete search history.

(56) References Cited

U.S. PATENT DOCUMENTS 5,840,024 A 11/1998 Taniguchi et al.
6,059,718 A 5/2000 Taniguchi et al.
8,195,277 B2 * 6/2012 Minai et al. ................... 600/424
8,251,890 B2 * 8/2012 Tanaka .......................... 600/103
2007/0238922 A1 * 10/2007 Oda et al. ...................... 600/117

(Continued)

FOREIGN PATENT DOCUMENTS

EP 2 082 678 A1 7/2009
JP 06-175771 6/1994

(Continued)

OTHER PUBLICATIONS

International Search Report dated Oct. 4, 2011 issued in PCT/JP2011/064225.

(Continued)

*Primary Examiner* — John P Leubecker
(74) *Attorney, Agent, or Firm* — Scully, Scott, Murphy & Presser, P.C.

(57) ABSTRACT

A probe shape detection apparatus includes a magnetic field sensing section for sensing a magnetic field generated by an electromagnetic coil in a flexible probe, a movement speed calculation section for calculating a movement speed of the coil, a coordinate computation section for calculating three-dimensional coordinates of the coil based on the sensed magnetic field, a moving average coordinate calculation section for calculating moving average coordinates of the coil, a comparison section for comparing the calculated movement speed with a predetermined threshold, a coil coordinate setting section for setting one of the moving average coordinates and the three-dimensional coordinates calculated by the coordinate computation section as the three-dimensional coordinates of the coil, based on a comparison result of the calculated moving speed, and a signal processing section for generating a video signal to display a shape of the probe, based on the set three-dimensional coordinates of the coil.

13 Claims, 12 Drawing Sheets

(56) References Cited

U.S. PATENT DOCUMENTS

2007/0238987 A1* 10/2007 Minai et al. .................. 600/424
2009/0221869 A1*  9/2009 Tanaka ......................... 600/103
2009/0237073 A1*  9/2009 Uchiyama et al. ....... 324/207.11
2012/0157825 A1*  6/2012 Koyrakh et al. .............. 600/424

FOREIGN PATENT DOCUMENTS

| JP | 07-111968 | 5/1995 |
| JP | 08-107875 | 4/1996 |
| JP | 2003-245243 | 9/2003 |
| JP | 2008-119260 | 5/2008 |

OTHER PUBLICATIONS

European Search Report dated May 31, 2013 from corresponding European Application No. 11 80 0671.7.

* cited by examiner

○ : SENSE COIL FACING X AXIS DIRECTION

◐ : SENSE COIL FACING Y AXIS DIRECTION

○ : SENSE COIL FACING Z AXIS DIRECTION

PROBE SHAPE DETECTION APPARATUS AND PROBE SHAPE DETECTION METHOD

CROSS REFERENCE TO RELATED APPLICATION

This application is a continuation application of PCT/JP2011/064225 filed on Jun. 22, 2011 and claims benefit of Japanese Application No. 2010-151410 filed in Japan on Jul. 1, 2010, the entire contents of which are incorporated herein by this reference.

BACKGROUND OF THE INVENTION

1. Field of the Invention

The present invention relates to a probe shape detection apparatus and a probe shape detection method which detect a probe shape of a flexible probe.

2. Description of the Related Art

Recently, medical instruments such as endoscopes have come to be used widely to perform procedures for examination and treatment in a body cavity.

An endoscope insertion portion shape detection apparatus is sometimes used to detect a shape of a flexible endoscope insertion portion as a probe shape by detecting a position of each of plural electromagnetic coils arranged along a longitudinal direction of the endoscope insertion portion in order to facilitate insertion into a winding body cavity such as a large intestine.

A first conventional example, namely an endoscope insertion portion shape detection apparatus disclosed in Japanese Patent Application Laid-Open Publication No. 2008-119260, is configured to measure a moving speed of a source coil placed on a most proximal side of source coils serving as plural electromagnetic coils which generate magnetic fields by being arranged in a longitudinal direction of an endoscope insertion portion.

The first conventional example discloses a technique for controlling a display period of insertion aid information used to support insertion operation of the endoscope insertion portion, according to the source coil moving speed by setting a correction coefficient used to correct a time during which the insertion aid information is displayed, based on results of the measurement.

Also, a second conventional example, namely an endoscope insertion portion shape detection apparatus disclosed in Japanese Patent Application Laid-Open Publication No. 2003-245243, is configured to detect noise in plural frequency groups using sense coils adapted to detect positions of plural source coils arranged in an endoscope insertion portion, with the source coils stopped being driven. The second conventional example discloses a technique for driving the plural source coils with a drive signal of the frequency group containing the lowest noise based on noise detection results.

SUMMARY OF THE INVENTION

A probe shape detection apparatus according to one aspect of the present invention includes: a magnetic field sensing section adapted to sense a magnetic field generated when an alternating current signal is applied to an electromagnetic coil provided in a probe having flexibility; a movement speed calculation section adapted to calculate a movement speed of the electromagnetic coil; a coordinate computation section adapted to perform a computational operation to calculate three-dimensional coordinates which represent a position of the magnetic field coil based on the magnetic field sensed by the magnetic field sensing section; a moving average coordinate calculation section adapted to calculate moving average coordinates within a predetermined period based on a plurality of sets of three-dimensional coordinates of the electromagnetic coil detected by the coordinate computation section within the predetermined period; a comparison section adapted to compare the movement speed calculated by the movement speed calculation section with a predetermined threshold; a coil coordinate setting section adapted to set the moving average coordinates as the three-dimensional coordinates of the electromagnetic coil when a comparison result produced by the comparison section indicates that the movement speed is lower than the predetermined threshold and set the three-dimensional coordinates calculated by the coordinate computation section as the three-dimensional coordinates of the electromagnetic coil when the comparison result indicates that the movement speed is higher than the predetermined threshold; and a signal processing section adapted to generate a video signal to display a shape of the probe, based on the three-dimensional coordinates of the electromagnetic coil set by the coil coordinate setting section.

A probe shape detection method according to one aspect of the present invention includes: a magnetic field sensing step in which a magnetic field sensing section senses a magnetic field generated when an alternating current signal is applied to an electromagnetic coil provided in a probe having flexibility; a movement speed calculation step in which a movement speed calculation section calculates a movement speed of the electromagnetic coil; a coordinate computation step in which a coordinate computation section performs a computational operation to calculate three-dimensional coordinates which represent a position of the magnetic field coil based on the magnetic field sensed by the magnetic field sensing step; a moving average coordinate calculation step in which a moving average coordinate calculation section calculates moving average coordinates within a predetermined period based on a plurality of sets of three-dimensional coordinates of the electromagnetic coil detected by the coordinate computation step within the predetermined period; a comparison step in which a comparison section compares the movement speed calculated by the movement speed calculation step with a predetermined threshold; a coil coordinate setting step in which a coil coordinate setting section sets the moving average coordinates as the three-dimensional coordinates of the electromagnetic coil when a comparison result produced by the comparison step indicates that the movement speed is lower than the predetermined threshold and sets the three-dimensional coordinates calculated by the coordinate computation section as the three-dimensional coordinates of the electromagnetic coil when the comparison result indicates that the movement speed is higher than the predetermined threshold; and a signal processing step in which a signal processing section generates a video signal to display a shape of the probe, based on the three-dimensional coordinates of the electromagnetic coil set by the coil coordinate setting section.

BRIEF DESCRIPTION OF THE DRAWINGS

FIG. 5 is a block diagram showing a configuration of the receiver block and the like;

FIG. 6 is an operation timing chart of a two-port memory and the like;

DETAILED DESCRIPTION OF THE PREFERRED EMBODIMENTS

Embodiments of the present invention will be described below with reference to the drawings.

(First Embodiment)

Figure 1:
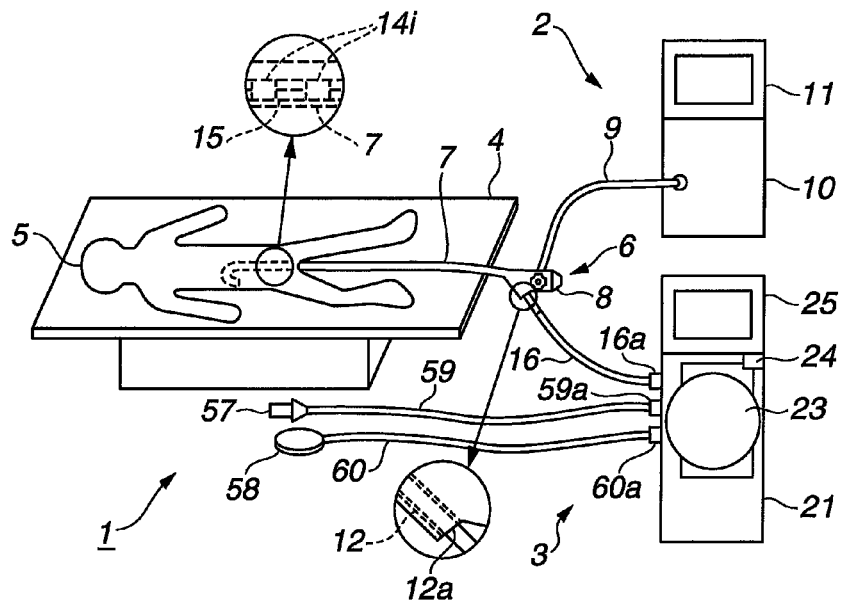
FIG. 1 is a diagram showing an overall configuration of an endoscope system equipped with a first embodiment of the present invention.

As shown in FIG. 1, an endoscope system 1 equipped with a first embodiment includes an endoscope apparatus 2 used for endoscopy and an endoscope insertion portion shape detection apparatus 3 serving as a probe shape detection apparatus used to aid endoscopy. The endoscope insertion portion shape detection apparatus 3 is used as an insertion aid by modeling and displaying a shape of an endoscope insertion portion 7 serving as a probe of an electronic endoscope 6 when a surgeon conducts endoscopy by inserting the endoscope insertion portion 7 into a body cavity of a patient 5 lying on a bed 4.

The electronic endoscope 6 includes the endoscope insertion portion 7 which is an elongated probe having flexibility. An operation section 8 with a bending operation knob provided thereon is formed on a rear end of the endoscope insertion portion 7. A universal code 9 is extended out from the operation section 8 and connected to a video processor 10.

Figure 13:
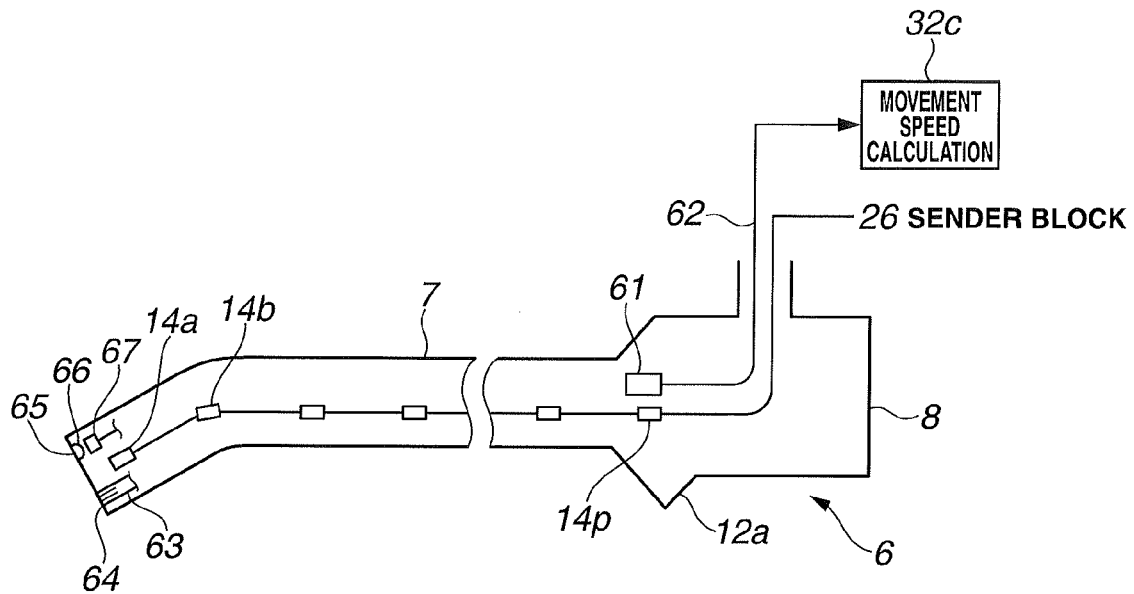
FIG. 13 is a diagram showing a schematic configuration of an electronic endoscope according to a second modification.

A light guide 63 (see FIG. 13 described later) is passed through the electronic endoscope 6. As shown in FIG. 13, the light guide 63 transmits illuminating light from a light source section in the video processor 10 and emits the transmitted illuminating light from an illuminating window 64 provided at a distal end of the endoscope insertion portion 7 to illuminate a diseased part and the like. An object such as the illuminated diseased part and the like is focused by an objective lens 66 mounted in an observation window 65 provided next to the illuminating window 64 into an optical image on an image pickup device 67 placed at an image forming location of the objective lens 66. Then, the optical image is subjected to photoelectric conversion by the image pickup device 67.

A signal resulting from the photoelectric conversion is subjected to signal processing by a video signal processing section (not shown) in the video processor 10 shown in FIG. 1, and a standard video signal is generated, which is then displayed on an image observation monitor 11 connected to the video processor 10.

A treatment instrument channel 12 is provided in the electronic endoscope 6. A probe 15 with, for example, sixteen source coils 14a, 14b, ..., 14p (hereinafter represented by a reference character 14i) placed therein is passed through an insertion port 12a of the treatment instrument channel 12, thereby placing the source coils 14i in the endoscope insertion portion 7, where the source coils 14i serve as electromagnetic coils which have the functionality of magnetic field generating devices.

Incidentally, the source coils 14i may be placed in the endoscope insertion portion 7 at predetermined intervals along a longitudinal direction of the endoscope insertion portion 7 without placing the source coils 14i in the probe 15 (such a configuration example is shown in FIG. 13).

A source cable 16 extends out from a rear end of the probe 15, and a connector 16a at a rear end of the source cable is detachably connected to a detection apparatus 21 of the endoscope insertion portion shape detection apparatus 3.

When alternating current signals serving as drive signals are applied to the source coils 14i serving as magnetic field generating devices from the side of the detection apparatus 21 via the source cable 16, magnetic fields are generated around the source coils 14i.

In the detection apparatus 21 placed near the bed 4 on which the patient 5 is lying, a sense coil unit 23 making up magnetic field sensing means or a magnetic field sensing section adapted to sense magnetic fields of the source coils 14i is provided movably, for example, in a vertical direction (ascendably/descendably). Sense coils serving as plural magnetic field sensing devices are placed in the sense coil unit 23.

Figure 2:
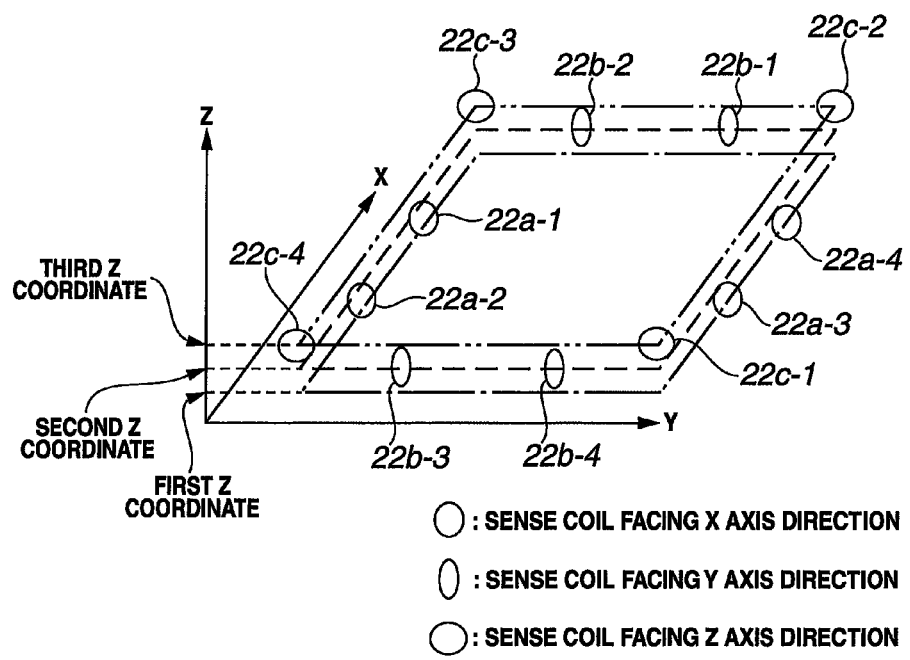
FIG. 2 is a diagram showing an exemplary arrangement of coils contained in a sense coil unit.

More specifically, as shown in FIG. 2, twelve sense coils are placed, including sense coils 22a-1, 22a-2, 22a-3, and 22a-4 which face, for example, an X axis and whose centers have, for example, a first Z coordinate; sense coils 22b-1, 22b-2, 22b-3, and 22b-4 which face a Y axis and whose centers have a second Z coordinate different from the first Z coordinate; and sense coils 22c-1, 22c-2, 22c-3, and 22c-4 which face a Z axis and whose centers have a third Z coordinate different from the first and second Z coordinates (hereinafter the sense coils will be referred to simply as 22a, 22b, ..., 22l and represented by a reference character 22j).

The sense coils 22j are connected to the detection apparatus 21 via a cable (not shown) from the sense coil unit 23. The detection apparatus 21 is provided with an operation panel 24 for use by a user to operate the apparatus.

Also, as shown in FIG. 1, a monitor 25 is placed on top of the detection apparatus 21, serving as display means which displays a scope model obtained by modeling a detected shape of the endoscope insertion portion 7.

Figure 3:
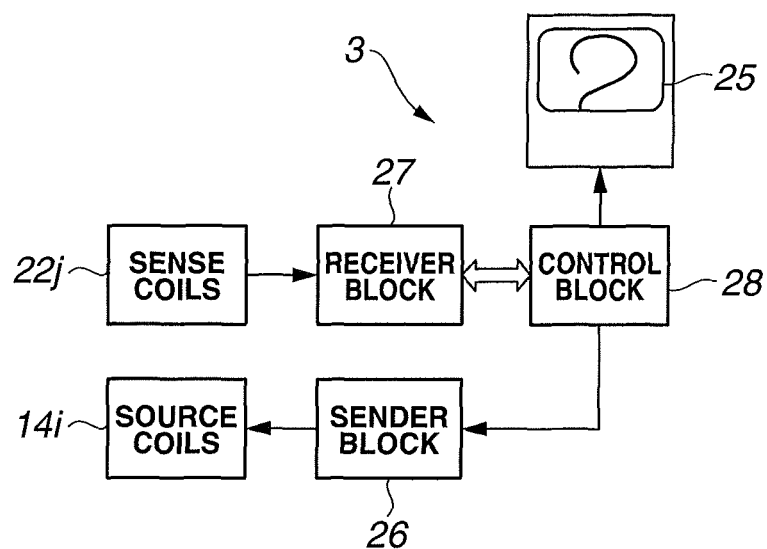
FIG. 3 is a block diagram showing a configuration of an endoscope insertion portion shape detection apparatus of FIG. 1.

As shown in FIG. 3, the endoscope insertion portion shape detection apparatus 3 includes a sender block 26 adapted to send drive signals to the source coils 14i and thereby drive the source coils 14i, a receiver block 27 adapted to perform signal processing on signals sensed (received) by the sense coils 22j in the sense coil unit 23, and a control block 28 adapted to perform signal processing on output signals from the receiver block 27.

Figure 4:
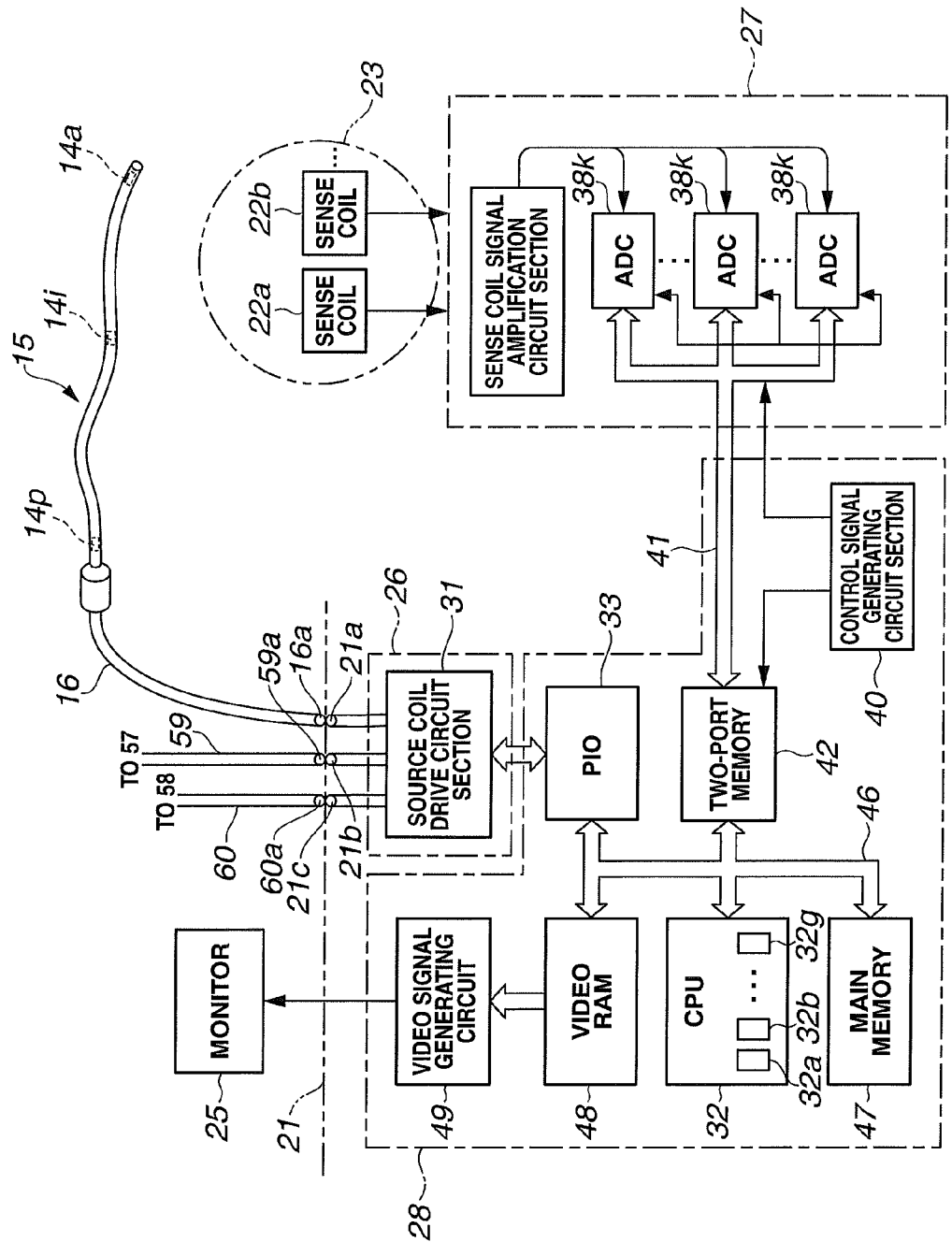
FIG. 4 is a diagram showing a configuration of a receiver block and control block of FIG. 3.

As shown in FIG. 4, the sixteen source coils 14$i$ intended to generate magnetic fields are placed at predetermined intervals as described above in the probe 15 installed in the endoscope insertion portion 7. The source coils 14$i$ are connected to a source coil drive circuit section 31 of the sender block 26, where the source coil drive circuit section 31 is adapted to generate sixteen drive signals (alternating current signals) differing from one another in frequency. The source coil drive circuit section 31 drives the respective source coils 14$i$ with respective sine wave drive signals differing from one another in frequency. Incidentally, as described later in FIG. 10A, the sender block 26 includes oscillator circuits 51$a$ to 51$p$ and transformers 52$a$ to 52$p$.

On the other hand, the twelve sense coils 22$j$ in the sense coil unit 23 are connected to a sense coil signal amplification circuit section 34 of the receiver block 27.

Figure 5:
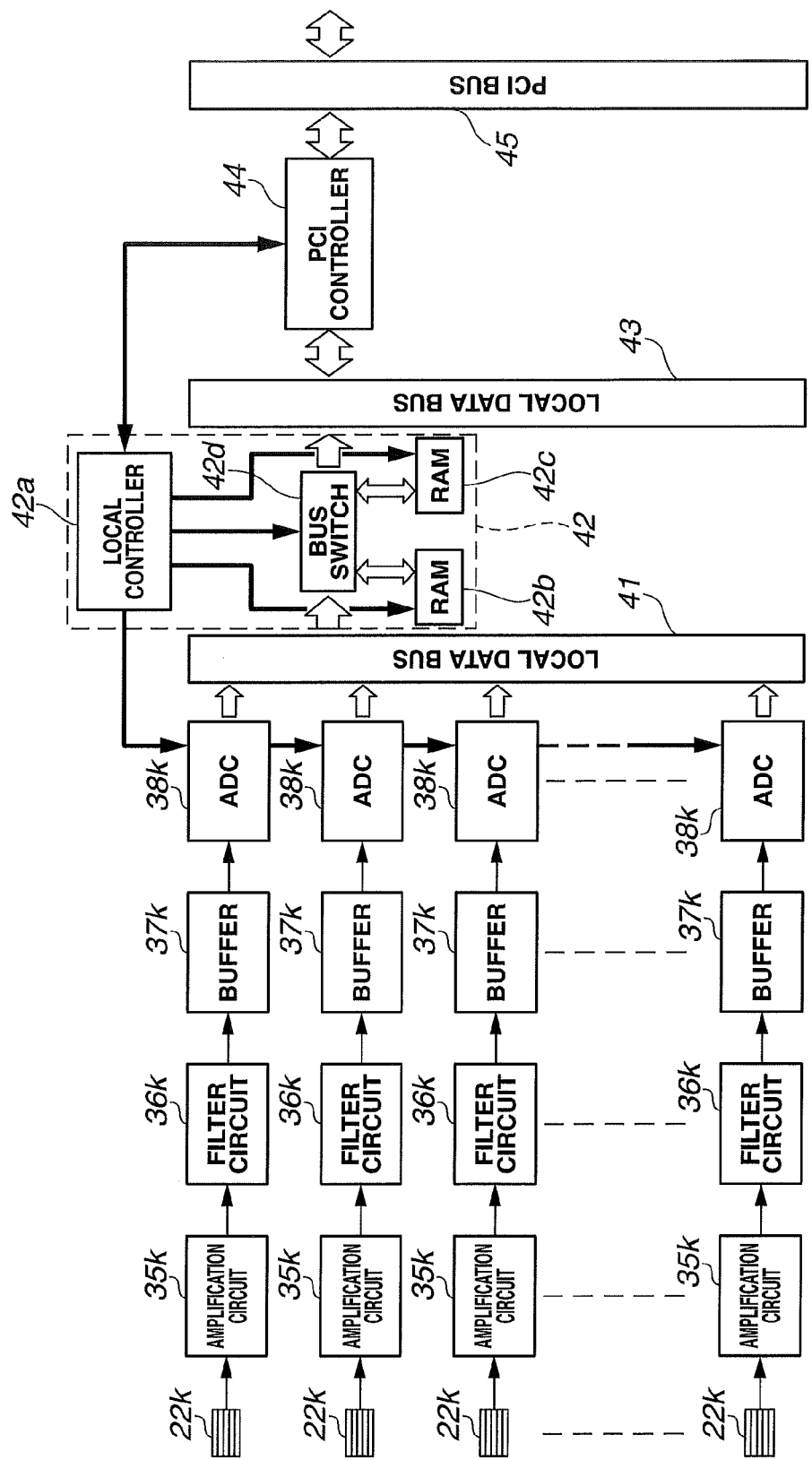

In the sense coil signal amplification circuit section 34, as shown in FIG. 5, twelve single-core coils 22$k$ of the sense coils 22$j$ are connected to respective amplification circuits 35$k$, making up twelve receiver processing systems. Consequently, minute signals detected by the respective single-core coils 22$k$ are amplified by the amplification circuits 35$k$.

The amplified signals are passed through filter circuits 36$k$ with band-pass characteristics capable of passing plural frequencies generated by the source coils 14$i$, and consequently unnecessary frequency components other than the pass-bands are removed. Then, after being outputted to buffers 37$k$, the signals are converted by ADCs (analog-digital converters) 38$k$ into digital signals readable by the control block 28.

The receiver block 27 in FIG. 4 is made up of the sense coil signal amplification circuit section 34 and the ADCs 38$k$. The sense coil signal amplification circuit section 34 in turn is made up of the amplification circuits 35$k$, filter circuits 36$k$, and the output buffers 37$k$.

As shown in FIG. 4, twelve outputs of the sense coil signal amplification circuit section 34 are transmitted to the twelve ADCs 38$k$ and converted into digital data with a predetermined sampling period by clocks supplied from a control signal generating circuit section 40 in the control block 28. The digital data is written into a two-port memory 42 via a local data bus 41 by a control signal from the control signal generating circuit section 40.

In functional terms, the two-port memory 42 includes a local controller 42$a$, a first RAM 42$b$, a second RAM 42$c$, and a bus switch 42$d$ as shown in FIG. 5.

Figure 6:
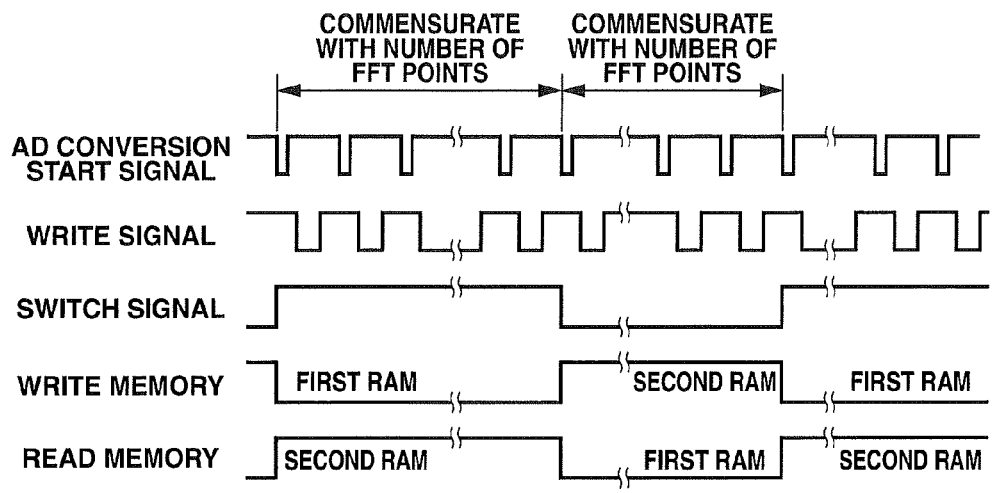

Using timing such as shown in FIG. 6, the ADCs 38$k$ start A/D conversion at an A/D conversion start signal from the local controller 42$a$. Also, at a switch signal from the local controller 42$a$, the bus switch 42$d$ switches between the RAMs 42$b$ and 42$c$ to use the first RAM 42$b$ and the second RAM 42$c$ alternately as a read memory and a write memory. In this way, once power is turned on, data is captured constantly under a write signal.

As shown in FIG. 4, a CPU (central processing unit) 32, which makes up the control block 28 and performs computational processes including calculations of an endoscope insertion portion shape as described later, reads digital data (of the signals sensed by the sense coils 22$j$) written into the two-port memory 42 at a control signal from the control signal generating circuit section 40, via internal buses 46 including a local data bus 43, a PCI controller 44, and a PCI bus 45 (see FIG. 5).

Figure 7:
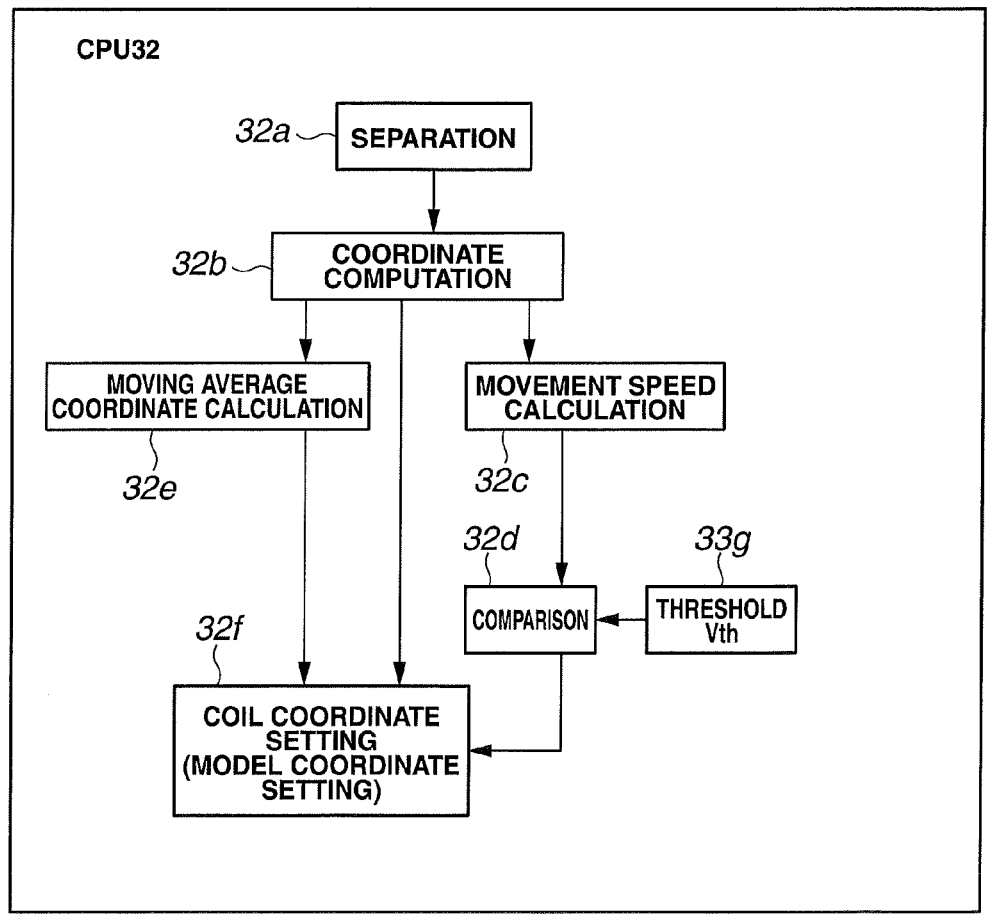
FIG. 7 is a diagram showing processing functions of a CPU making up the control block.

FIG. 7 shows processing functions of the CPU 32. The CPU 32 functions as a separation section 32$a$ adapted to perform a frequency extraction process (specifically, a fast Fourier transform: FFT) on the digital data using a main memory 47 shown in FIG. 4 and separate (extract) the digital data into magnetic field detection data having frequency components corresponding to drive frequencies of the respective source coils 14$i$.

The CPU 32 also functions as a coordinate computation section 32$b$ adapted to calculate three-dimensional coordinates of the respective source coils 14$i$ provided in the endoscope insertion portion 7 of the electronic endoscope 6 from respective items of the magnetic field detection data separated by the separation section 32$a$.

Also, the CPU 32 functions as a movement speed calculation section 32$c$ adapted to calculate movement speed of at least one of the source coils 14$i$ based on amounts of movement of the source coil 14$i$ per unit time at plural sets of three-dimensional coordinates calculated by the coordinate computation section 32$b$ within an appropriate period. The period here may be set equal to a predetermined period used to calculate moving average coordinates. Also, an average value of respective movement speeds of plural source coils 14$i$ instead of one source coil 14$i$ may be calculated and used as the movement speed.

Also, the CPU 32 functions as a comparison section 32$d$ adapted to compare the movement speed calculated by the movement speed calculation section 32$c$ with a predetermined threshold Vth (for movement speed) (e.g., 900 mm/sec).

Incidentally, the CPU 32 has a threshold storage section 32$g$ (simply abbreviated to threshold Vth in FIG. 7) used to store the predetermined threshold Vth. The threshold storage section 32$g$ may be provided outside the CPU 32. Also, the CPU 32 functions as a moving average coordinate calculation section 32$e$ adapted to calculate moving average coordinates within a predetermined period based on a plurality of sets of three-dimensional coordinates calculated for the respective source coils 14$i$ within the predetermined period.

Also, the CPU 32 functions as a coil coordinate setting section 32$f$ adapted to make a setting so as to use one of the moving average coordinates and the three-dimensional coordinates calculated by the coordinate computation section 32$b$, as the three-dimensional coordinates (referred to as model coordinates) of the respective source coils 14$i$ used to generate and display the endoscope insertion portion shape, based on a comparison result produced by the comparison section 32$d$.

More specifically, the coil coordinate setting section 32$f$ makes a setting so as to use the moving average coordinates as the model coordinates of the source coils 14$i$ when the movement speed is lower than the predetermined threshold Vth, or makes a setting so as to use the individual sets of three-dimensional coordinates calculated by the coordinate computation section 32$b$ as the model coordinates of the source coils 14$i$ when the movement speed is equal to or higher than the predetermined threshold Vth.

Then, using data of the model coordinates set by the coil coordinate setting section 32$f$ so as to be used in generating the endoscope insertion portion shape, the CPU 32 generates display data for use as a scope model corresponding to the shape of the endoscope insertion portion 7 and outputs the display data to a video RAM 48.

A video signal generating circuit 49 reads the display data written in the video RAM 48, converts the display data into an analog video signal, and outputs the video signal to the monitor 25.

Upon accepting the analog video signal as input, the monitor 25 displays a scope model of the endoscope insertion portion 7 of the electronic endoscope 6 on a display screen.

The CPU 32 calculates magnetic field detection information on each of the source coils 14i, i.e., an electromotive force (amplitude value of a sine wave signal) generated in the single-core coil 22k of each sense coil 22j and phase data. Incidentally, the phase data, which includes polarity of the electromotive force, provides information on a distance from the sense coil 22j to the source coil 14i whose three-dimensional coordinates are calculated.

Also, according to the present embodiment, as shown in FIG. 1, an in-vitro marker 57 and a reference plate 58 may be connected to the detection apparatus 21 and used, where the in-vitro marker 57 is used to display an extracorporeal position in order to check a position of the endoscope insertion portion 7 inserted into the body or for other purposes while the reference plate 58 is, for example, attached to the abdomen or the like of the patient 5 and used to always display the scope model from a specific direction (of the patient 5) even if a body posture of the patient 5 changes. Incidentally, if the body posture of the patient 5 does not change, the position of the in-vitro marker 57 remains almost unchanged.

One source coil is contained in the in-vitro marker 57, and a connector 59a at a proximal end of a cable 59 of the in-vitro marker 57 is detachably connected to the detection apparatus 21.

When the connector 59a is connected, the source coil in the in-vitro marker 57 is driven as in the case of the source coils 14i in the probe 15, and a position of the source coil in the in-vitro marker 57 detected by the sense coil unit 23 is displayed on the monitor 25 as with the scope model.

Also, for example, three source coils are placed on a disk surface in a disk-shaped portion of the reference plate 58, and a connector 60a at a proximal end of a cable 60 connected to the three source coils is detachably connected to the detection apparatus 21.

As positions of the three source coils are detected, a plane in which the three source coils are placed is determined The plane is used to draw such a scope model that is observed when the endoscope insertion portion 7 is viewed in a direction perpendicular to the plane.

Also, according to the present embodiment, as shown in FIG. 4, the detection apparatus 21 is provided with connector receptacles 21a, 21b, and 21c connected, respectively, with the connector 16a of the probe 15, the connector 59a of the in-vitro marker 57, and the connector 60a of the reference plate 58. Each of the receptacles 21a, 21b, and 21c is connected to the source coil drive circuit section 31.

Figure 10A:
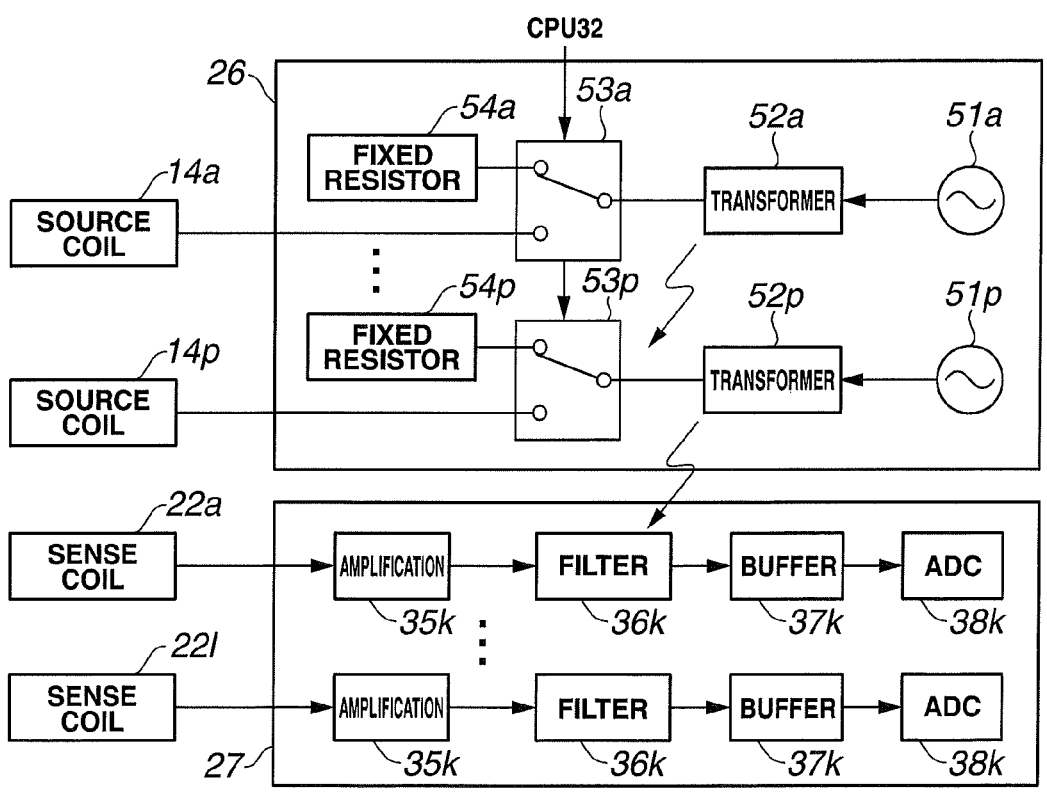
FIG. 10A is a block diagram showing a configuration of a sender block and a receiver block according to a second embodiment of the present invention in a state in which fixed resistors are driven.

Also, the CPU 32 controls operation and the like of the oscillator circuits 51i (see FIG. 10A described later in a second embodiment) of the source coil drive circuit section 31 via a PIO (parallel input/output circuit) 33 connected to the internal buses 46. However, according to the present embodiment, selector switches 53i and fixed resistors 54i in FIG. 10 are not provided.

The endoscope insertion portion shape detection apparatus 3 serving as the probe shape detection apparatus configured as described above includes the sense coil unit 23 and the coordinate computation section 32b, where the sense coil unit 23 is made up of the plural sense coils 22j serving as magnetic field sensing means adapted to sense the magnetic fields generated when alternating current signals are applied to the source coils 14i serving as electromagnetic coils provided in the endoscope insertion portion 7 serving as a probe having flexibility while the coordinate computation section 32b serves as coordinate computation means adapted to perform computational operations to calculate three-dimensional coordinates which represent positions of the electromagnetic coils based on the magnetic fields sensed by the magnetic field sensing means.

Also, the endoscope insertion portion shape detection apparatus 3 includes the movement speed calculation section 32c and the moving average coordinate calculation section 32e, where the movement speed calculation section 32c serves as movement speed calculation means adapted to calculate the movement speed of the electromagnetic coils based on detection signal by the three-dimensional coordinates calculated by the coordinate computation section 32b (or signals sensed by sensors described later) while the moving average coordinate calculation section 32e serves as moving average coordinate calculation means adapted to calculate moving average coordinates within a predetermined period based on the plurality of sets of three-dimensional coordinates of the electromagnetic coils detected by the coordinate computation section 32b within the predetermined period.

Also, the endoscope insertion portion shape detection apparatus 3 includes the comparison section 32d and the coil coordinate setting section 32f, where the comparison section 32d serves as comparison means adapted to compare the movement speed calculated by the movement speed calculation section 32c with a predetermined threshold while the coil coordinate setting section 32f serves as coil coordinate setting means adapted to make a setting so as to use one of the moving average coordinates and the three-dimensional coordinates calculated by the coordinate computation section 32b, as the three-dimensional coordinates of the electromagnetic coils, based on a comparison result produced by the comparison section 32d.

Figure 8:
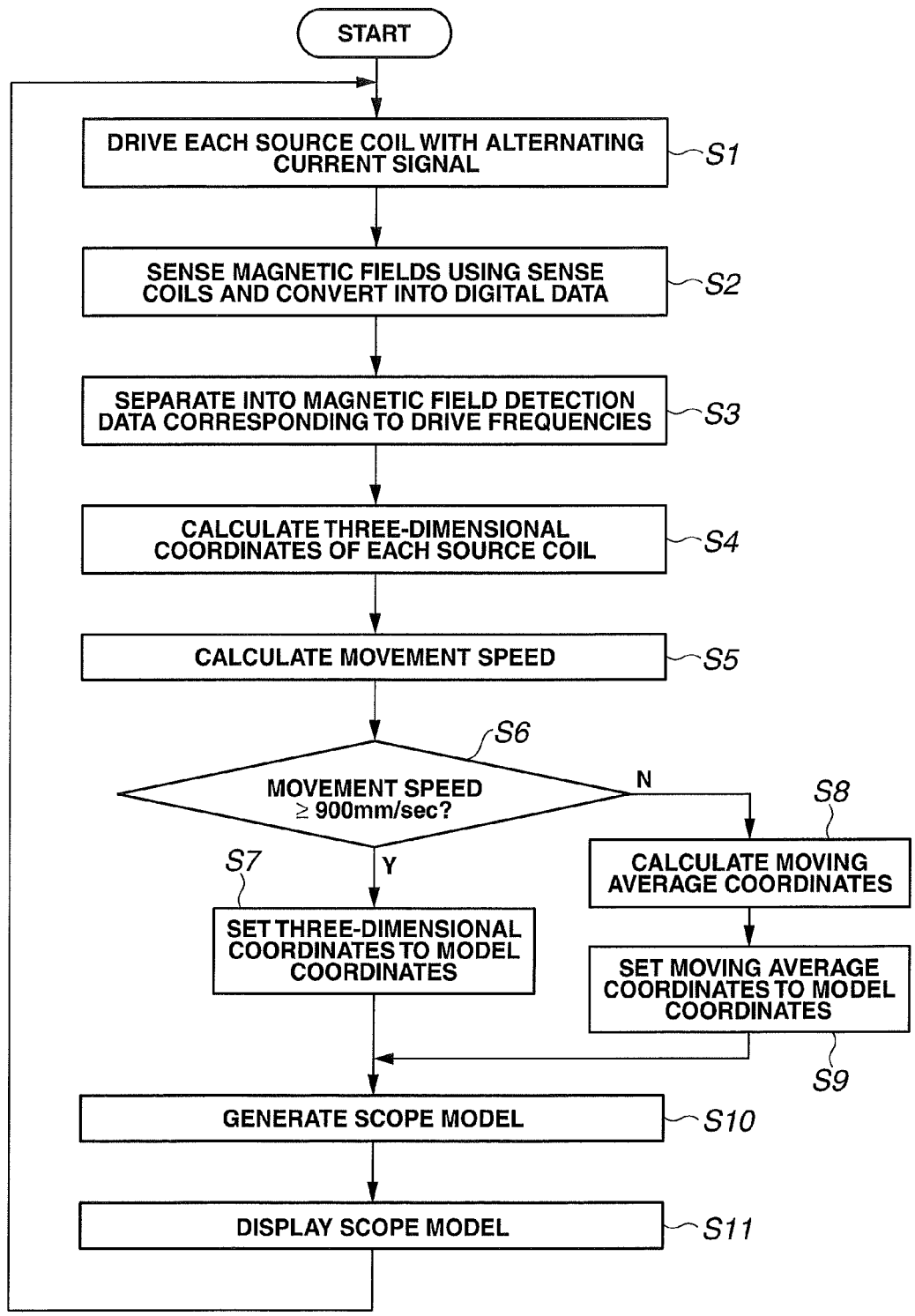
FIG. 8 is a flowchart showing processing procedures of a detection method for an endoscope insertion portion shape.

Description will be given of endoscope insertion portion shape detection operation performed by the endoscope insertion portion shape detection apparatus 3 configured as described above. FIG. 8 shows processing procedures of an endoscope insertion portion shape detection method performed by the endoscope insertion portion shape detection apparatus 3 according to the present embodiment.

As shown in FIG. 1, a nurse or the like connects the electronic endoscope 6 to the video processor 10 and connects the connector 16a at the rear end of the probe 15 installed in the treatment instrument channel 12 of the electronic endoscope 6 to the detection apparatus 21.

After the video processor 10 and detection apparatus 21 are turned on, the surgeon starts endoscopy of the patient 5 using the electronic endoscope 6. As shown in FIG. 3, the CPU 32 making up the control block 28 in the detection apparatus 21 causes the sender block 26 and receiver block 27 to start operating.

Then, as shown in Step 51 of FIG. 8, the sender block 26 drives the source coils 14i with respective alternating current signals differing from one another in drive frequency, causing each of the source coils 14i to generate a magnetic field.

Also, as shown in Step S2, the magnetic fields generated by the respective source coils 14i are sensed by the plural sense coils 22j of the sense coil unit 23 serving as magnetic field sensing means, and the sense coils 22j outputs sensed signals to the receiver block 27.

The receiver block 27 amplifies the inputted signals, filters the signals so as to pass only signals in predetermined frequency bands, then converts the signals into digital data by AID conversion, and sends the digital data to the CPU 32.

In Step S3, the CPU 32 by means of function of the separation section 32a performs an FFT process on the digital data and thereby separates the digital data into magnetic field detection data having frequency components corresponding to the drive frequencies of the respective source coils 14i.

Also, in Step S4, the CPU 32 by means of function of the coordinate computation section 32b performs computational operations to calculate three-dimensional coordinates of the respective source coils 14i provided in the endoscope insertion portion 7 from respective items of the separated magnetic field detection data. In doing so, the CPU 32 calculates the three-dimensional coordinates of the respective source coils 14i by referring to the phase data of magnetic field detection data.

Also, in Step S5, the CPU 32 by means of function of the movement speed calculation section 32c calculates the movement speed of, for example, one of the source coils 14i based on the plurality sets of three-dimensional coordinates calculated for the source coil 14i by the coordinate computation section 32b within a predetermined time.

Also, in Step S6, the CPU 32 by means of function of the comparison section 32d compares the movement speed calculated by the movement speed calculation section 32c with a predetermined threshold Vth (e.g., 900 mm/sec).

If a comparison process in Step S6 reveals that the actual calculated movement speed is equal to or higher than 900 mm/sec, the CPU 32 by means of function of the coil coordinate setting section 32f makes a setting in Step S7 such that the three-dimensional coordinates calculated by the coordinate computation section 32b will be used as model coordinates, and then the CPU 32 goes to the process of Step S10.

On the other hand, if the actual calculated movement speed is less than 900 mm/sec, the CPU 32 by means of function of the moving average coordinate calculation section 32e calculates the respective moving average coordinates of the three-dimensional coordinates of the respective source coils 14i in Step S8.

Then, in Step S9, the CPU 32 by means of function of the coil coordinate setting section 32f sets the moving average coordinates to be used as model coordinates, and then the CPU 32 goes to the process of Step S10.

Also, in Step S10, using data of the model coordinates set by means of function of the coil coordinate setting section 32f, the CPU 32 generates display data to be displayed as a scope model corresponding to the shape of the endoscope insertion portion 7. Then, the CPU 32 outputs the generated display data of the scope model to the video RAM 48.

In Step S11, the video signal generating circuit 49 reads the display data written in the video RAM 48, converts the display data into an analog video signal, and outputs the video signal to the monitor 25. Consequently, the scope model is displayed on the monitor 25. After the process of Step S11, the CPU 32 returns to the process of Step S1 and repeats the processes described above.

Incidentally, the process of Step S8 does not always need to be performed after a determination result is obtained in Step 6 as shown in FIG. 8, and may be performed, for example, simultaneously with the process of calculating the movement speed in Step S5.

The endoscope insertion portion shape detection method as a probe shape detection method according to the present embodiment shown in FIG. 8 includes Step S2 as a magnetic field sensing step of sensing magnetic fields generated when alternating current signals are applied to the source coils 14i as electromagnetic coils provided in the endoscope insertion portion 7 as a probe having flexibility.

Also, the endoscope insertion portion shape detection method includes Step S4 as a coordinate computation step of performing a computational operation to calculate three-dimensional coordinates which represent positions of the electromagnetic coils based on the magnetic fields sensed by the magnetic field sensing step, and Step S5 as a movement speed calculation step of calculating the movement speed of the electromagnetic coils based on the three-dimensional coordinates calculated by the coordinate computation step (or on signals sensed by a sensor described later).

Also, the endoscope insertion portion shape detection method includes Step S8 as a moving average coordinate calculation step of calculating moving average coordinates within a predetermined period based on a plurality of sets of three-dimensional coordinates of the electromagnetic coils detected by the coordinate computation step within the predetermined period, and Step S6 as a comparison step of comparing the movement speed calculated by the movement speed calculation step with a predetermined threshold.

Also, the endoscope insertion portion shape detection method includes Steps S7 and S9 as a coil coordinate setting step of making a setting so as to use one of the moving average coordinates and the three-dimensional coordinates calculated by the coordinate computation step, as the three-dimensional coordinates of the electromagnetic coils, according to comparison results produced by the comparison step.

Figure 9:
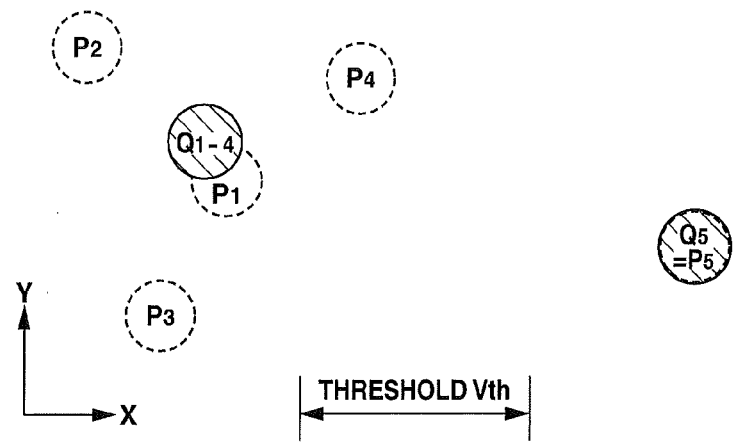
FIG. 9 is an explanatory diagram showing an example of three-dimensional coordinates calculated by a coordinate computation section and model coordinates actually used for model display.

FIG. 9 shows how a scope model is displayed according to the detection method in FIG. 8. Specifically, FIG. 9 shows positions P1, P2, P3, P4, and P5 (indicated schematically by dotted circles) of time-sequential three-dimensional coordinates of, for example, the most distal source coil 14a calculated sequentially at predetermined time intervals, i.e., at times t1, t2, t3, t4, and t5 as well as model coordinates Q1-4 and Q5 adopted to actually display a scope model indicated by oblique lines. FIG. 9 also shows magnitude of the threshold Vth in this case.

In FIG. 9, at positions P1 to P4, the movement speed is less than the threshold Vth. In this case, moving average coordinates (P1+ . . . +P4)/4 are adopted as the model coordinates Q1-4. In contrast, at the position P5 at time t5, since the calculated movement speed is equal to or higher than the threshold Vth, the three-dimensional coordinates of the position P5 are used as the model coordinates Q5 (without finding a moving average).

That is, when the movement speed is less than the threshold Vth, if the moving average coordinates are adopted as model coordinates, even if a detected (calculated) position fluctuates due to noise, it is possible to display a reliable scope model by reducing amounts of the fluctuations.

On the other hand, when the movement speed is equal to or higher than the threshold Vth, individual sets of three-dimensional coordinates are adopted as model coordinates. In this case, since moving average coordinates are not adopted, the scope model can be displayed without decreases in the response speed. Therefore, when the surgeon performs a maneuver, for example, to insert the endoscope insertion portion 7 deeper into the body cavity, the scope model can be displayed with a smaller time delay in responding to the maneuver.

Thus, the present embodiment provides the endoscope insertion portion shape detection apparatus 3 and an endoscope insertion portion shape detection method suitable for acquiring the endoscope insertion portion shape corresponding to the movement speed of the endoscope insertion portion 7 serving as a probe while reducing noise impacts.

Incidentally, if moving average coordinates are used alone regardless of the movement speed instead of setting model coordinates according to the movement speed as with the present embodiment, the moving average coordinates obtained by taking a moving average of positions P2 to P5 are adopted instead of the model coordinates Q5 in FIG. 9. This results in a reduced response speed.

The use of moving average coordinates according to the present embodiment is not limited to the case shown in FIG. 9, and other types of moving average coordinates may be used as long as the average is taken of two or more sets of three-dimensional coordinates differing in time. In such a case, the surgeon may be allowed to select/set a value of the predetermined period over which a time average is taken.

Also, plural different thresholds (e.g., 0<Vth<Vth2) may be set instead of a single value of the threshold Vth, and the value of the predetermined period used for the moving averaging may be changed according to magnitude relationships given by comparisons between the movement speed V calculated by the movement speed calculation section 32c and the thresholds Vth and Vth2.

In the case of FIG. 9, for example, a moving average of four sets of three-dimensional coordinates is taken in sequence, but the predetermined period may be set so as to take a moving average of three sets of three-dimensional coordinates. Alternatively, the predetermined period may be set so as to take a moving average of five or more sets of three-dimensional coordinates.

(Second Embodiment)

Figure 10B:
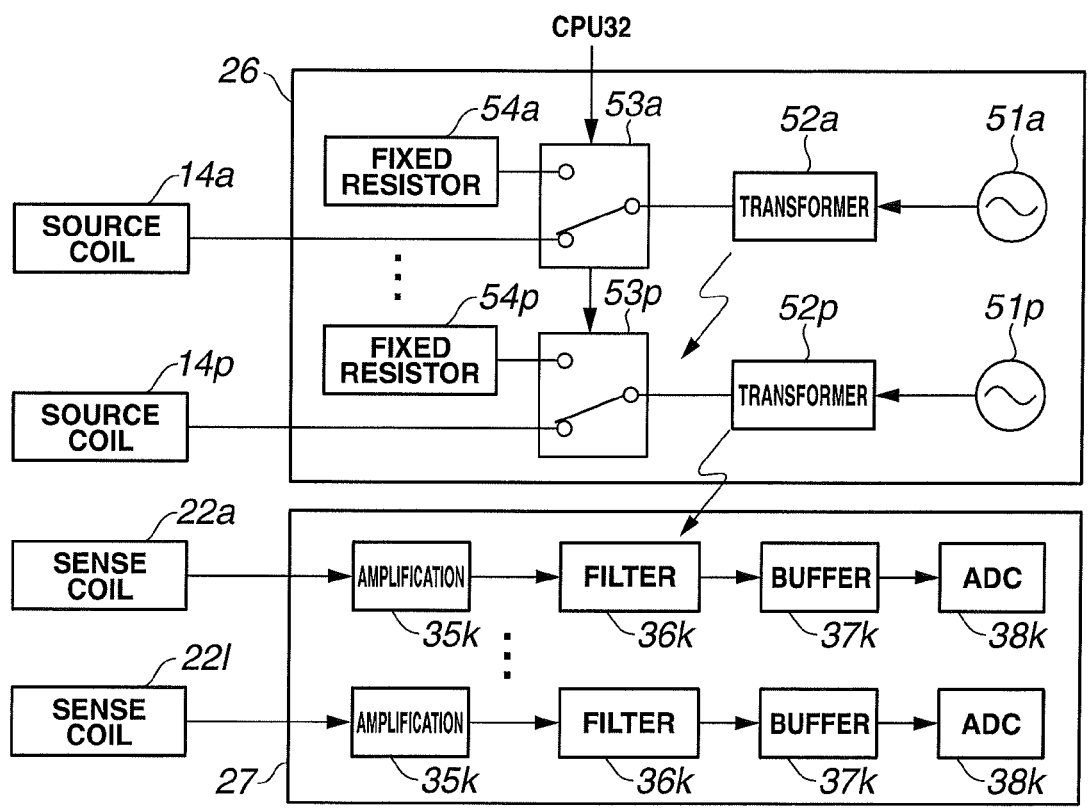
FIG. 10B is a block diagram showing a configuration of the sender block and the receiver block according to the second embodiment of the present invention in a state in which source coils are driven.

Next, a second embodiment of the present invention will be described. FIGS. 10A and 10B show configurations of the sender block 26 and the receiver block 27 according to the second embodiment of the present invention in a state of an amount-of-noise measurement period and in a state of an endoscope insertion portion shape detection period.

According to the present embodiment, selector switches 53i and fixed resistors 54i of amount-of-noise measurement means are provided in the sender block 26 according to the first embodiment. Incidentally, the amount-of-noise measurement means is made up of the selector switches 53i and the fixed resistors 54i as well as the receiver block 27 and the control block 28 described below.

During detection of an endoscope insertion portion shape, noise which can reduce detection accuracy is sometimes caused by leakage magnetic fields mixing into the side of the sense coils 22j or the receiver block 27 which uses the sense coils 22j from transformers 52i used to insulate the drive signals (alternating current signals) generated by the oscillator circuits 51i of the sender block from the side of the oscillator circuits 51i.

Also, noise produced by electrical equipment and the like used in an examination room where endoscopy is conducted will mix into the sense coils 22j or the receiver block 27 which uses the sense coils 22j and will sometimes reduce detection accuracy. The leakage magnetic fields from the transformers 52i can be reduced to some extent by magnetic shielding means, but weight of the endoscope insertion portion shape detection apparatus will be increased if magnetic shielding means is provided sufficiently. This is incompatible with the need for size and weight reduction.

Whereas the first embodiment is configured such that alternating current signals as output signals of the oscillator circuits 51i are applied to the respective source coils 14i thorough the transformers 52i, according to the present embodiment, the selector switches 53i are provided to switch output signals of the transformers 52i selectively between the source coils 14i and fixed resistors 54i.

During the amount-of-noise measurement period in which amounts of noise are measured, the selector switches 53i are switched, for example, by the CPU 32 so as to select the fixed resistors 54i as shown in FIG. 10A. On the other hand, during the detection period in which the endoscope insertion portion shape is detected, the selector switches 53i are switched so as to select the source coils 14i as shown in FIG. 10B.

Even during the amount-of-noise measurement period, as when alternating current signals are applied to the source coils 14i, the receiver block 27 performs signal detection with respect to signals sensed by the sense coils 22j and outputs results to the control block 28.

Figure 11:
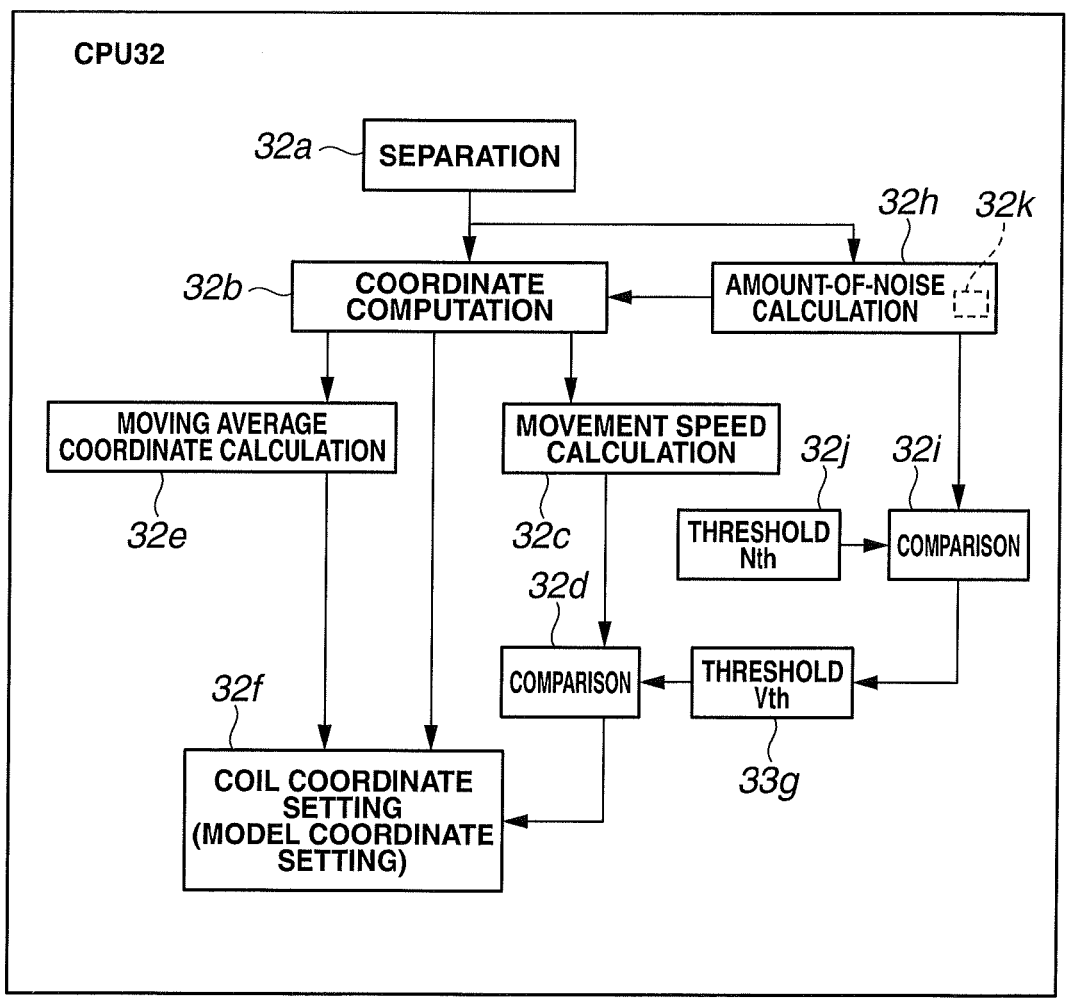
FIG. 11 is a diagram showing processing functions of a CPU making up the control block.

FIG. 11 shows processing functions of the CPU 32 making up the control block 28. In addition to the functions described in the first embodiment and shown in FIG. 7, the CPU 32 includes an amount-of-noise calculation section 32h adapted to calculate values (amplitude values) of the magnetic field detection data of the frequency components separated by the separation section 32a, as an amount of noise. Incidentally, the amount-of-noise calculation section 32h calculates, for example, an average value or the like of the magnetic field detection data of plural frequency components as the amount of noise. As described later, the amount of noise may be calculated based on the magnetic field detection data of a single frequency component.

The amount-of-noise calculation section 32h outputs the calculated amount of noise to a comparison section 32i for the amount of noise. The comparison section 32i compares the inputted amount of noise with an amount-of-noise threshold Nth stored in an amount-of-noise threshold storage section (simply abbreviated to threshold Nth in FIG. 11) 32j.

Based on comparison results, the comparison section 32i changes the value of the movement speed threshold Vth stored in the threshold storage section 32g. That is, the comparison section 32i functions as a threshold changing section adapted to change (the value of) the movement speed threshold Vth.

If the amount of noise calculated by the amount-of-noise calculation section 32h is equal to or larger than the amount-of-noise threshold Nth, the comparison section 32i establishes the same predetermined threshold Vth as the first embodiment. Thus, the coil coordinate setting section 33f sets model coordinates (coil coordinates) using the same predetermined threshold Vth as that of the first embodiment.

On the other hand, if the amount of noise calculated by the amount-of-noise calculation section 32h is less than the amount-of-noise threshold Nth, the comparison section 32i sets Vtha smaller than the threshold Vth and the coil coordinate setting section 33f sets model coordinates using the threshold Vtha.

When the amount of noise calculated by the amount-of-noise calculation section 32h is less than the amount-of-noise threshold Nth, the three-dimensional coordinates of the source coils 14i can be calculated with higher accuracy (than when the amount of noise is as large as the threshold Nth or above), and thus the comparison section 32i sets such a small threshold Vtha.

Also, the amount-of-noise calculation section 32h outputs the calculated amount of noise to the coordinate computation section 32b. When calculating the three-dimensional coordinates of the source coils 14i by actually driving the source coils 14i, the coordinate computation section 32b takes the amount of noise into consideration in calculating the three-dimensional coordinates.

For example, the amount of noise of a leakage magnetic field leaking from any of the transformers 52i has a same frequency component as the alternating current signal outputted from the oscillator circuit 51i and has a predetermined phase relationship with the oscillator circuit 51i. Consequently, the amount of noise has a substantially constant value over a duration of a period of the alternating current signal.

If the amount-of-noise calculation section 32h detects such an amount of noise, the coordinate computation section 32b subtracts the amount of noise when calculating the three-dimensional coordinates of the source coil 14$i$. This reduces impacts of the amount of noise caused by the leakage magnetic field from the transformer 52$i$.

On the other hand, if the amount-of-noise calculation section 32$h$ detects an amount of noise not correlated with the alternating current signal, the coordinate computation section 32$b$ may change display colors of the scope model as follows according to the amount of noise Nth' when calculating the three-dimensional coordinates of the source coils 14$i$.

For example, in displaying a scope model, the part of the endoscope insertion portion which corresponds to the source coils 14$i$ whose amounts of noise calculated by the amount-of-noise calculation section 32$h$ exceed the threshold Nth' may be displayed in a different color from the part whose amounts of noise are less than the threshold Nth'.

Incidentally, the fixed resistor 54$i$ according to the present embodiment is a resistor whose resistance value corresponds to an impedance value of the source coil 14$i$ at the drive frequency used when the alternating current signal is driven by the oscillator circuit 51$i$. That is, the fixed resistor 54$i$ is made up of a resistor with a sufficiently small inductance component and is almost insusceptible to any surrounding magnetic field.

Figure 12:
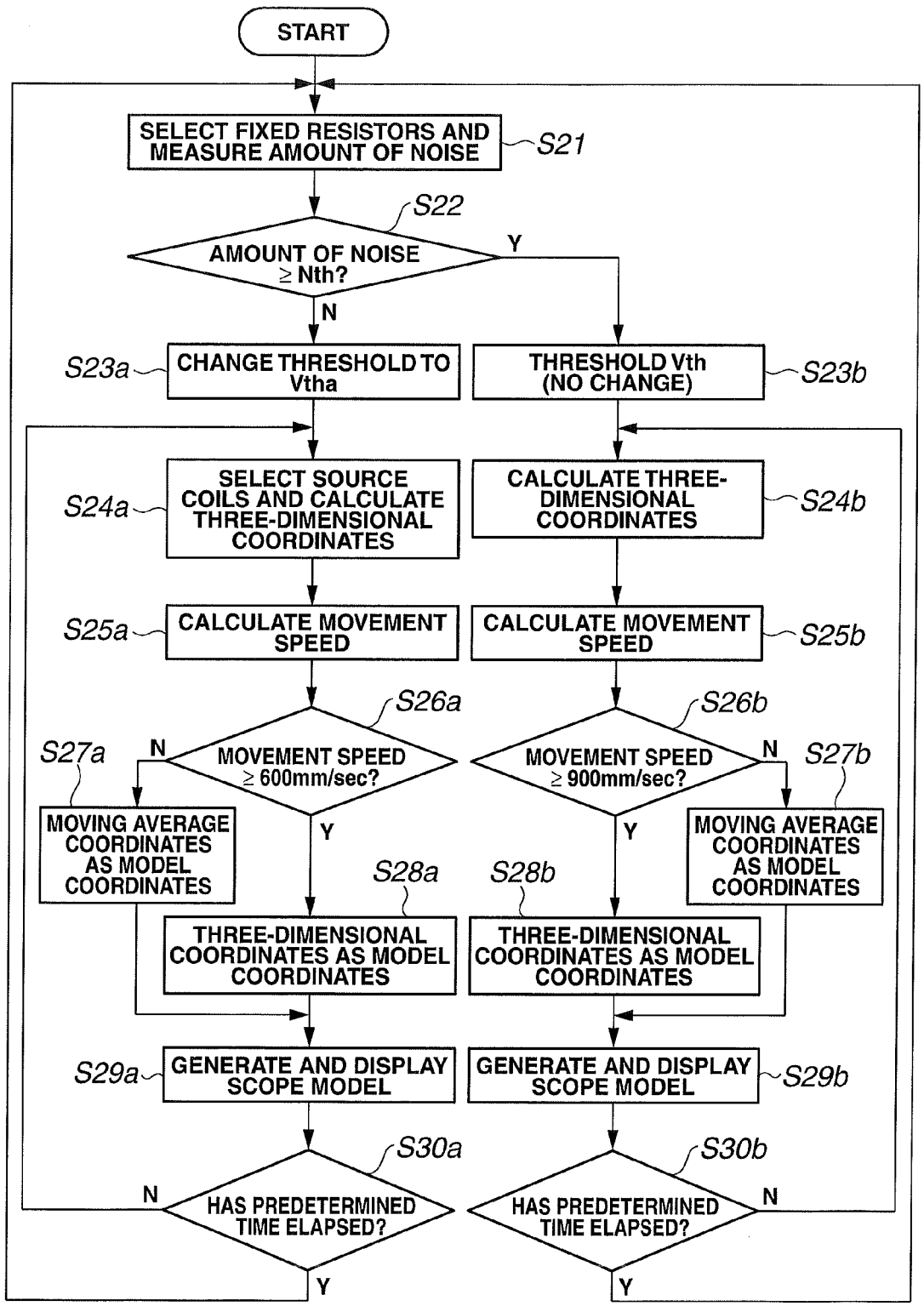
FIG. 12 is a flowchart showing processing procedures of a detection method for an endoscope insertion portion shape including an amount-of-noise measurement process.

Processing procedures according to the present embodiment are as shown in FIG. 12. When operation of the endoscope insertion portion shape detection apparatus 3 according to the present embodiment is started, first in Step S21, the CPU 32 switches the selector switches 53$i$ so as to select the fixed resistors 54$i$ as shown in FIG. 10A, and consequently the process of measuring the amounts of noise is performed.

Next, in Step S22, the amount-of-noise calculation section 32$h$ of the CPU 32 outputs the calculated amount of noise to the comparison section 32$i$, which then determines whether or not the calculated amount of noise is equal to or larger than the threshold Nth.

If the calculated amount of noise is not less than the threshold Nth, the comparison section 32$i$ changes (sets) the movement speed threshold Vth to a smaller threshold Vtha (e.g., 600 mm/sec) as shown in Step S23$a$. On the other hand, if the calculated amount of noise is less than the threshold Nth, the comparison section 32$i$ does not change the movement speed threshold Vth as shown in Step S23$b$.

After the process of Step S23$a$ or S23$b$, the CPU 32 switches the selector switches 53$i$ so as to select the source coils 14$i$ by changing from the fixed resistors 54$i$ in Steps S24$a$ or S24$b$. By the switching, detection of the endoscope insertion portion shape is started, and the CPU 32 performs the process of calculating three-dimensional positions of the source coils 14$i$.

Next, in Step S25$a$ or S25$b$, the CPU 32 performs the process of calculating the movement speed of the source coils 14$i$. Next, the CPU 32 determines whether or not the calculated movement speed is equal to or higher than the threshold: i.e., the threshold Vtha (600 mm/sec) in Step S26$a$, or the threshold Vth (900 mm/sec) in Step S26$b$.

If it is determined in Step S26$a$ that the calculated movement speed is less than 600 mm/sec, the CPU 32 performs the process of calculating moving average coordinates and setting the calculated moving average coordinates as model coordinates as shown in Step S27$a$. On the other hand, if the calculated movement speed is equal to or higher than 600 mm/sec, the CPU 32 performs the process of setting the three-dimensional coordinates as model coordinates as shown in Step S28$a$.

Similarly, if it is determined in Step S26$b$ that the calculated movement speed is less than 900 mm/sec, the CPU 32 performs the process of calculating moving average coordinates and setting the calculated moving average coordinates as model coordinates as shown in Step S27$b$. On the other hand, if the calculated movement speed is equal to or higher than 900 mm/sec, the CPU 32 performs the process of setting the three-dimensional coordinates as model coordinates as shown in Step S28$b$.

After the processes of Steps S27$a$ and S28$a$ or Steps S27$b$ and S28$b$, the CPU 32 performs the process of generating a scope model and displays the generated scope model in Step S29$a$ or S29$b$.

Next, in Steps S30$a$ or S30$b$, the CPU 32 determines whether or not a predetermined time has elapsed. If the predetermined time has not elapsed, the CPU 32 returns to Step S24$a$ from Step S30$a$, or to Step S24$b$ from Step S30$b$, and continues the process of detecting the endoscope insertion portion shape.

On the other hand, if the predetermined time has elapsed, the CPU 32 returns to the process of Step S21 from Step S30$a$ or from Step S30$b$. Then, the CPU 32 measures the amount of noise, and performs the process of detecting the endoscope insertion portion shape after the measurement. In this case, the surgeon may be allowed to select the predetermined time.

In addition to achieving the same operation and effects as those of the first embodiment, the present embodiment configured to operate as described above can measure the amounts of noise and then model and display the endoscope insertion portion shape based on the amounts of noise calculated as a result of the measurement.

Specifically, when the amount of noise is small, the three-dimensional coordinates of the source coils 14$i$ can be calculated (detected) accurately, making it possible to display a scope model with improved response speed (when the endoscope insertion portion 7 serving as a probe or the source coils 14$i$ are moved).

That is, when the amount of noise is small, since fluctuations can be suppressed, it is possible to display the scope model by improving the response speed accordingly. To give a concrete description using the threshold 900 mm/sec according to the first embodiment, since the amounts of noise are not measured in the first embodiment, the movement speed threshold Vth is set to 900 mm/sec to suppress fluctuations and prevent decreases in the response speed.

In this case, if the detected movement speed is, for example, 800 mm/sec, moving average coordinates are used as model coordinates to suppress fluctuations.

In contrast, according to the present embodiment, when the amount of noise is less than the (amount-of-noise) threshold Nth, since the fluctuations can be suppressed considerably, if the detected movement speed is, for example, 800 mm/sec (which is higher than the movement speed threshold Vtha of 600 mm/sec), the three-dimensional coordinates of the source coils 14$i$ instead of the moving average coordinates are used as model coordinates. This makes it possible to alleviate decreases in the response speed more efficiently while suppressing fluctuations.

Also, by repeating the operation of measuring the amounts of noise and maintaining detection of the shape of the endoscope insertion portion 7 for a predetermined time based on results of the measurement at predetermined time intervals and after the predetermined time measuring the amount of noise again, the present embodiment can appropriately deal with any variation in a noise amount level during endoscopy.

Also, according to the present embodiment, in measuring and calculating the amounts of noise, a configuration in which the selector switches 53$i$ are switched to the fixed resistors 54$i$ can be implemented relatively easily and the amounts of noise can be measured in a short period of time. There is no need for oscillations at frequencies other than the frequencies used for detection of the endoscope insertion portion shape unlike the conventional examples.

Therefore, even in the process of endoscopy, the amounts of noise can be calculated in a short period of time practically without adverse effects on the detection of the endoscope insertion portion shape, making it possible to acquire and display a highly reliable endoscope insertion portion shape.

Incidentally, although a case in which a single amount-of-noise threshold Nth is set has been described in the present embodiment, plural thresholds may be set and a movement speed threshold may be set at plural levels according to the calculated amount of noise.

Specifically, for example, by setting an amount-of-noise threshold Ntha smaller than the threshold Nth, if a calculated amount of noise is less than the threshold Ntha, a threshold Vthb still smaller than the movement speed threshold Vtha can be set. If actually detected movement speed is less than the threshold Vthb, moving average coordinates can be set as model coordinates. On the other hand, if the movement speed is equal to or higher than the threshold Vthb, three-dimensional coordinates can be set as model coordinates.

This makes it possible to acquire and display a scope model with further improved response speed while suppressing fluctuations.

Incidentally, although a configuration in which all the source coils 14a to 14p placed in the endoscope insertion portion 7 are switched is shown in FIGS. 10A and 10B, it is not necessary to switch all the source coils, and a configuration may be adopted in which one or a few source coils are switched.

Figure 10C:
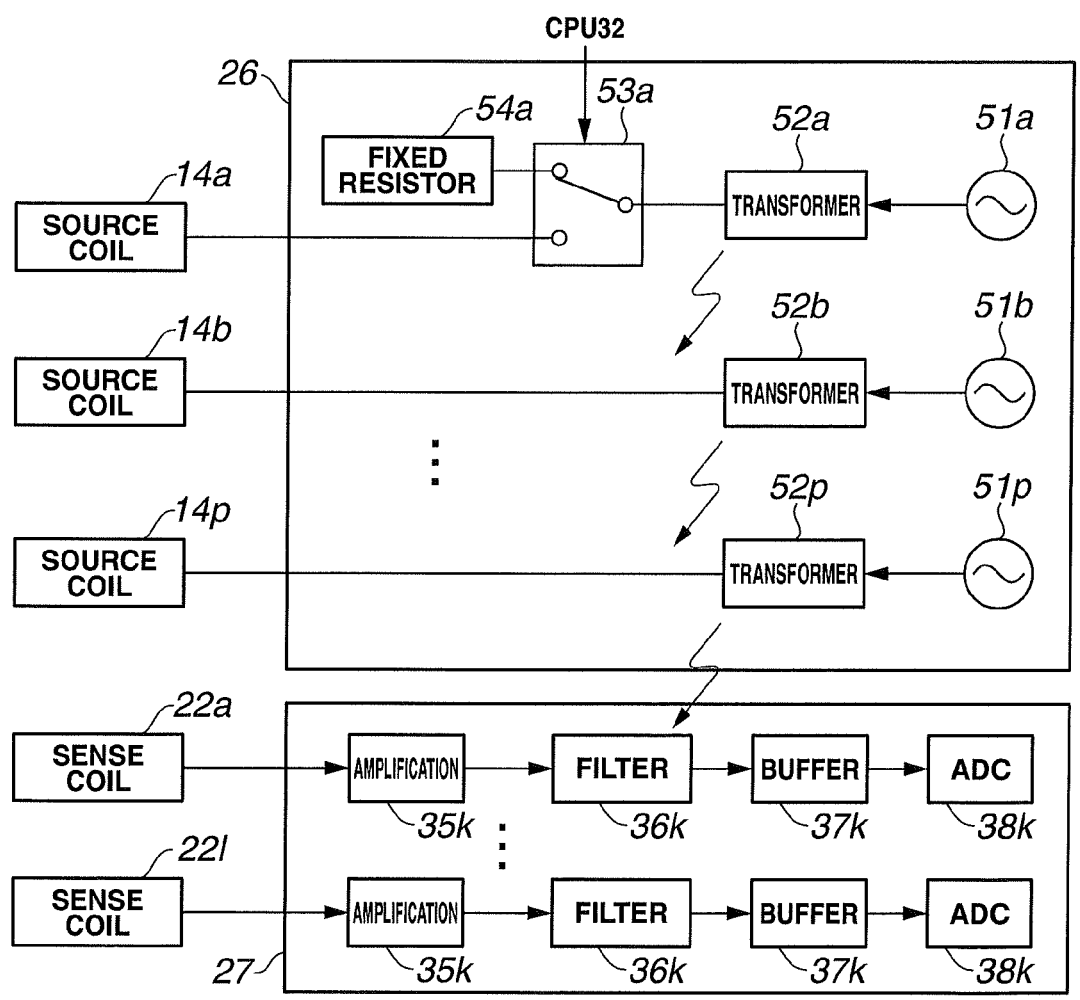
FIG. 10C is a block diagram showing a configuration of a sender block and a receiver block according to a first modification in a state in which fixed resistors are driven.

For example, a first modification shown in FIG. 10C is a configuration example in which only the source coil 14a which is a specific electromagnetic coil placed, for example, in a distal end portion of the endoscope insertion portion 7 is switched with the fixed resistor 54a.

The source coils 14b to 14p other than the source coil 14a are driven by alternating current signals, which are output signals of the oscillator circuits 51b to 51p, via the transformer 52b to 52p, respectively.

In this case, during the amount-of-noise measurement period, the amount-of-noise calculation section 32h calculates the value of the magnetic field detection data of the frequency component from the oscillator circuit 51 as the amount of noise. Then, the comparison section 32i compares the amount of noise with the threshold Nth.

In this case, since only the single source coil 14a is switched, amount-of-noise measurement means can be implemented easily. Also, even while the amount of noise is being measured (i.e., during an amount-of-noise measurement period), the endoscope insertion portion shape can be detected using the other source coils 14b to 14p.

Incidentally, during a period in which the fixed resistor 54a is selected, the three-dimensional coordinates of the source coil 14a cannot be detected, but the three-dimensional coordinates of the source coil 14a can be calculated by interpolation from the other source coils 14b to 14p.

In this way, according to the present modification, even while endoscopy is conducted, the measurement of the amounts of noise and detection of the endoscope insertion portion shape can be performed concurrently.

Incidentally, although in the embodiments described above, the movement speed of the source coils 14i placed in the endoscope insertion portion 7 is calculated from the three-dimensional coordinates of the source coils 14i, the movement speed may be calculated using a sensor as shown in FIG. 13.

In the example of FIG. 13, for example, an acceleration sensor 61 adapted to sense acceleration is provided at a proximal end of the endoscope insertion portion 7 or in the operation section 8. Via a signal line 62, the acceleration sensor 61 is connected to the movement speed calculation section 32c of the CPU 32 making up the control block 28 in the detection apparatus 21.

In this case, the movement speed calculation section 32c calculates a time integral of an acceleration sensing signal from the acceleration sensor 61 and thereby calculates the movement speed of the endoscope insertion portion 7, in other words, longitudinal movement speed of the endoscope insertion portion 7 as measured via the source coils 14i placed in the endoscope insertion portion 7. The movement speed calculation section 32c outputs information about the calculated movement speed to the comparison section 32d (see FIG. 11).

Since the movement speed is calculated using a sensor, the present modification has the advantage that noise impacts can be reduced more easily than when the movement speed is calculated from the three-dimensional coordinates of the source coils 14i.

Also, in an exemplary configuration of a second modification shown in FIG. 13, the source coils 14i are arranged at predetermined intervals along the longitudinal direction of the endoscope insertion portion 7 of the electronic endoscope 6. Alternatively, as in the case of the first embodiment, the source coils 14i may be detachably placed in the electronic endoscope 6. Incidentally, as in the case of a third modification shown in FIG. 14, the movement speed threshold Vth may be changed and set according to the amount of noise calculated by the amount-of-noise calculation section 32h.

The smaller the amount of noise is, the higher the accuracy or reliability of the three-dimensional coordinates of the source coils 14i is. Therefore, the movement speed threshold Vth may be made smaller as the amount of noise decreases. In this case, as shown in FIG. 14, the movement speed threshold Vth may be set according to magnitude (evaluation value) of an amount of dispersion in three-dimensional position based on the amount of noise.

Figure 14:
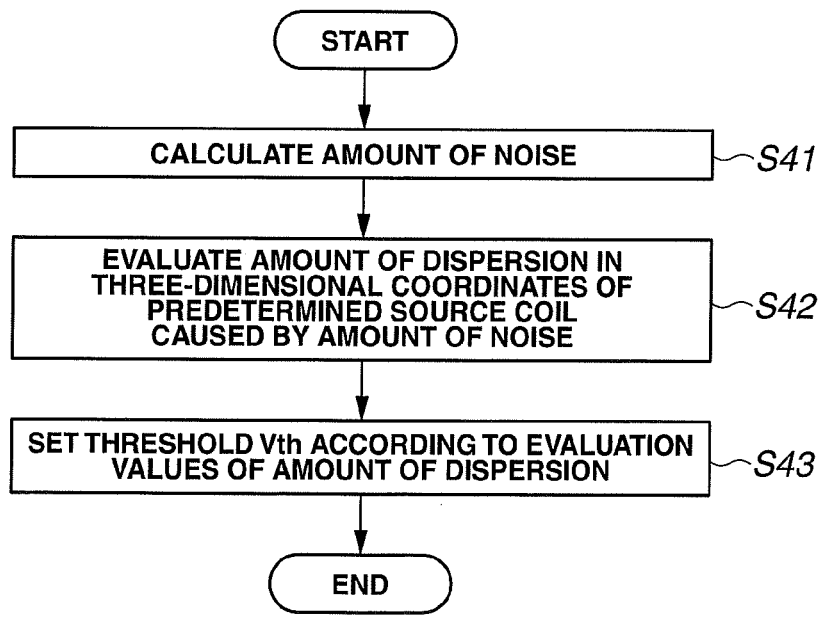
FIG. 14 is a flowchart showing processing procedures for a threshold change setting according to a third modification.

The modification described in FIG. 14 includes evaluation means adapted to evaluate the amount of dispersion in three-dimensional position based on the amount of noise (specifically, an evaluation section 32k serving as evaluation means can be provided as indicated by dotted lines in the amount-of-noise calculation section 32h of the CPU 32 shown in FIG. 11). Then, the threshold Vth is changed and set according to the evaluation value of the amount of dispersion in a three-dimensional position when the evaluation value is produced by the evaluation means.

First in Step S41 shown in FIG. 14, the CPU 32 by means of function of the amount-of-noise calculation section 32h calculates an amount of noise No. In this case, the CPU 32 calculates the amount of noise No with respect to a fixed resistor 54q (omitted from illustration) switched from a predetermined source coil 14q as described below.

Next, in Step S42, the CPU 32 by means of function of the coordinate computation section 32b evaluates the amount of dispersion in the three-dimensional position of the predetermined source coil 14q using (the magnitude of) the calculated amount of noise No, where the dispersion is caused by the amount of noise.

As the predetermined source coil 14q, the source coil in the in-vitro marker 57 is used, for example. The source coil is fixed to a body surface of the patient 5, and thus hardly changes its location. This makes it possible to appropriately evaluate the amount of dispersion in the three-dimensional position caused by the amount of noise. Incidentally, the source coil may be fixed at such a location near the body surface of the patient 5 that is not changed even if the body posture of the patient 5 changes.

The amount of dispersion in the three-dimensional position of the source coil is evaluated when magnetic field detection data is taken (calculated) as Do+No and Do−No by taking into consideration the impacts of the amount of noise No on the magnetic field detection data Do acquired in the latest state from the source coil 14q.

If the evaluation values of three-dimensional position (i.e., position for which a range of the amount of dispersion is determined) corresponding to the magnetic field detection data of Do+No and Do−No are, for example, $P_+$ and $P_-$, respectively, the CPU 32 changes and sets (determines) the threshold Vth according to the evaluation values of the amount of dispersion in Step S43 next.

The CPU 32 by means of function of a threshold changing and setting section sets the threshold Vth based on the absolute value $|P_+ - P_-|$ of the difference between the evaluation values, in other words, the evaluation values of the amount of dispersion of the three-dimensional coordinates, and thereby finishes the threshold changing and setting process. Then, processes similar to those in FIG. 12 are performed using the threshold Vth.

As an application example of FIG. 14, when a scope model is displayed by being updated on every display cycle, the movement speed threshold Vth may be set to the magnitude of the evaluation value of the amount of dispersion in three-dimensional position due to the calculated amount of noise on each display cycle.

Incidentally, when the amount of noise is measured using a source coil 14q other than the source coils 14i placed in the endoscope insertion portion 7, a configuration may be adopted in which one selector switch selectively switches between one source coil 14q and one fixed resistor.

Regarding the source coils 14i placed in the endoscope insertion portion 7, such a configuration as in the first embodiment may be used. In that case, the detection of the endoscope insertion portion shape and measurement of the amount of noise can be performed concurrently, as with the case described in FIG. 10C. Also, in that case, the three-dimensional coordinates of all the source coils 14a to 14p placed in the endoscope insertion portion 7 can be calculated.

On the other hand, the amount of noise may be measured by selecting, as appropriate, one or more of the source coils 14i placed in the endoscope insertion portion 7 as the source coil(s) 14q used in the process of FIG. 14.

Note that embodiments configured by combining parts of the embodiments and the like described above are also included in the present invention.

What is claimed is:

1. A probe shape detection apparatus comprising:
a magnetic field sensing section adapted to sense a magnetic field generated when an alternating current signal is applied to an electromagnetic coil provided in a probe having flexibility;
a movement speed calculation section adapted to calculate a movement speed of the electromagnetic coil;
a coordinate computation section adapted to perform a computational operation to calculate three-dimensional coordinates which represent a position of the electromagnetic coil based on the magnetic field sensed by the magnetic field sensing section;
a moving average coordinate calculation section adapted to calculate moving average coordinates within a predetermined period based on a plurality of sets of three-dimensional coordinates of the electromagnetic coil detected by the coordinate computation section within the predetermined period;
a comparison section adapted to compare the movement speed calculated by the movement speed calculation section with a predetermined threshold;
a coil coordinate setting section adapted to set the moving average coordinates as the three-dimensional coordinates of the electromagnetic coil when a comparison result produced by the comparison section indicates that the movement speed is lower than the predetermined threshold and set the three-dimensional coordinates calculated by the coordinate computation section as the three-dimensional coordinates of the electromagnetic coil when the comparison result indicates that the movement speed is higher than the predetermined threshold; and
a signal processing section adapted to generate a video signal to display a shape of the probe, based on the three-dimensional coordinates of the electromagnetic coil set by the coil coordinate setting section.

2. The probe shape detection apparatus according to claim 1, further comprising:
an amount-of-noise measurement section adapted to measure an amount of noise produced when the alternating current signal is applied to the electromagnetic coil; and
a threshold changing section adapted to change the predetermined threshold according to a measurement result produced by the amount-of-noise measurement section.

3. The probe shape detection apparatus according to claim 2, further comprising:
a fixed resistor; and
a switching section adapted to switch between the electromagnetic coil and the fixed resistor so as to selectively supply the alternating current signal to one of the electromagnetic coil and the fixed resistor, wherein
when the alternating current signal is being supplied to the fixed resistor by the switching section, the amount-of-noise measurement section measures a signal generated based on the magnetic field sensing section, as an amount of noise.

4. The probe shape detection apparatus according to claim 3, wherein the fixed resistor is capable of being selectively switchable with a specific electromagnetic coil out of a plurality of the electromagnetic coils provided in the probe; and during a period in which the amount-of-noise measurement section selects the fixed resistor and the amount of noise is measured, an alternating current signal is applied to the plurality of electromagnetic coils other than the specific electromagnetic coil to allow three-dimensional coordinates of the plurality of electromagnetic coils other than the specific electromagnetic coil to be calculated.

5. The probe shape detection apparatus according to claim 2, wherein the coil coordinate setting section makes a setting so as to use the moving average coordinates as the three-dimensional coordinates of the electromagnetic coil when the movement speed is lower than the predetermined threshold, and makes a setting so as to use the three-dimensional coordinates calculated by the coordinate computation section, as the three-dimensional coordinates of the electromagnetic coil when the movement speed is equal to or higher than the predetermined threshold.

6. The probe shape detection apparatus according to claim 2, wherein the threshold changing section compares the amount of noise measured by the amount-of-noise measurement section with a preset threshold for the amount of noise, and sets the predetermined threshold to a threshold smaller than the predetermined threshold when the amount of noise is less than the threshold for the amount of noise, and uses the predetermined threshold when the amount of noise is equal to or larger than the threshold for the amount of noise.

7. The probe shape detection apparatus according to claim 2, further comprising an evaluation section adapted to evaluate an amount of dispersion in a three-dimensional position of the electromagnetic coil caused by the amount of noise, based on the amount of noise measured by the amount-of-noise measurement section.

8. The probe shape detection apparatus according to claim 7, wherein the threshold changing section changes and sets the predetermined threshold according to an evaluation value of the amount of dispersion in the three-dimensional position, the evaluation value being produced by the evaluation section.

9. The probe shape detection apparatus according to claim 1, wherein the coil coordinate setting section makes a setting so as to use the moving average coordinates as the three-dimensional coordinates of the electromagnetic coil when the movement speed is lower than the predetermined threshold, and makes a setting so as to use the three-dimensional coordinates calculated by the coordinate computation section, as the three-dimensional coordinates of the electromagnetic coil when the movement speed is equal to or higher than the predetermined threshold.

10. A method of actuating a probe shape detection apparatus comprising:
 a magnetic field sensing step in which a magnetic field sensing section senses a magnetic field generated when an alternating current signal is applied to an electromagnetic coil provided in a probe having flexibility;
 a movement speed calculation step in which a movement speed calculation section calculates a movement speed of the electromagnetic coil;
 a coordinate computation step in which a coordinate computation section performs a computational operation to calculate three-dimensional coordinates which represent a position of the electromagnetic coil based on the magnetic field sensed by the magnetic field sensing step;
 a moving average coordinate calculation step in which a moving average coordinate calculation section calculates moving average coordinates within a predetermined period based on a plurality of sets of three-dimensional coordinates of the electromagnetic coil detected by the coordinate computation step within the predetermined period;
 a comparison step in which a comparison section compares the movement speed calculated by the movement speed calculation step with a predetermined threshold;
 a coil coordinate setting step in which a coil coordinate setting section sets the moving average coordinates as the three-dimensional coordinates of the electromagnetic coil when a comparison result produced by the comparison step indicates that the movement speed is lower than the predetermined threshold and sets the three-dimensional coordinates calculated by the coordinate computation section as the three-dimensional coordinates of the electromagnetic coil when the comparison result indicates that the movement speed is higher than the predetermined threshold; and
 a signal processing step in which a signal processing section generates a video signal to display a shape of the probe, based on the three-dimensional coordinates of the electromagnetic coil set by the coil coordinate setting section.

11. The method of actuating the probe shape detection apparatus according to claim 10, wherein the coil coordinate setting step makes a setting so as to use the moving average coordinates as the three-dimensional coordinates of the electromagnetic coil when the movement speed is lower than the predetermined threshold, and makes a setting so as to use the three-dimensional coordinates calculated by the coordinate computation step, as the three-dimensional coordinates of the electromagnetic coil when the movement speed is equal to or higher than the predetermined threshold.

12. The method of actuating the probe shape detection apparatus according to claim 11, further comprising an amount-of-noise measurement step of switching from the electromagnetic coil to a fixed resistor with a resistance value substantially equal to impedance of the electromagnetic coil and measuring the magnetic field sensed by the magnetic field sensing step, as an amount of noise when the alternating current signal is applied to the fixed resistor.

13. The method of actuating the probe shape detection apparatus according to claim 12, further comprising a threshold setting step of comparing the amount of noise measured by the amount-of-noise measurement step with a preset threshold for the amount of noise, and setting the predetermined threshold to a threshold smaller than the predetermined threshold when the amount of noise is less than the threshold for the amount of noise, and making a setting so as not to change the predetermined threshold when the amount of noise is equal to or larger than the threshold for the amount of noise.

* * * * *